(12) United States Patent
Wang et al.

(10) Patent No.: US 7,838,642 B2
(45) Date of Patent: Nov. 23, 2010

(54) PROCESS FOR THE PREPARATION OF SUCRALOSE BY THE DEACYLATION OF TRICHLOROSUCROSE-6-ETHYL ESTER

(75) Inventors: Fei Wang, Nanjing (CN); Haibing He, Nanjing (CN); Jinshan Wu, Yancheng (CN); Xin Yang, Nanjing (CN); Yongzhu Yu, Nanjing (CN); Zhisong Fan, Nanjing (CN)

(73) Assignee: JK Sucralose Inc., Yancheng, Jiangsu Province (CN)

( * ) Notice: Subject to any disclaimer, the term of this patent is extended or adjusted under 35 U.S.C. 154(b) by 589 days.

(21) Appl. No.: 11/746,264

(22) Filed: May 9, 2007

(65) Prior Publication Data
US 2008/0221313 A1   Sep. 11, 2008

(51) Int. Cl.
*C07H 1/00* (2006.01)
(52) U.S. Cl. .................................... 536/18.4
(58) Field of Classification Search ............ 536/18.4
See application file for complete search history.

(56) References Cited

U.S. PATENT DOCUMENTS 4,380,476 A * 4/1983 Mufti et al. ............... 127/46.3
4,980,463 A * 12/1990 Walkup et al. ............. 536/124
6,809,198 B2  10/2004 El Kabbani et al.
6,890,581 B2 * 5/2005 Vernon et al. ............. 426/658

FOREIGN PATENT DOCUMENTS

EP        0043649 A1    1/1982
JP        57-46995      3/1982

OTHER PUBLICATIONS

Greene T.W. et al, Protective Groups in Organic Synthesis, Wiley, $3^{rd}$ edn., 1999, pp. 701-702, 705-706 and 713.*

* cited by examiner

*Primary Examiner*—Shaojia Anna Jiang
*Assistant Examiner*—Ganapathy Krishnan
(74) *Attorney, Agent, or Firm*—Occhiuti Rohlicek & Tsao LLP

(57) ABSTRACT

The present invention discloses a process for the preparation of sucralose by the deacylation of trichlorosucrose-6-ethyl ester, wherein the deacylation reaction is performed in an alcohol solvent in the presence of organic base catalyst, so as to obtain sucralose.

5 Claims, No Drawings

PROCESS FOR THE PREPARATION OF SUCRALOSE BY THE DEACYLATION OF TRICHLOROSUCROSE-6-ETHYL ESTER

CROSS-REFERENCE TO RELATED APPLICATIONS

This application is being filed as a U.S. Utility application which claims the benefit of Chinese Patent Application No. 200710085647.9, filed on Mar. 6, 2007, the contents of which is hereby incorporated by reference in its entirety.

FIELD OF THE INVENTION

The present invention relates to the synthesis of sucralose by the deacylation of trichlorosucrose-6-ethyl ester (4,1',6-trichloro-4,1',6-trideoxy-6-acetylgalactosylsucrose).

BACKGROUND OF THE INVENTION

As a novel sweetener, sucralose is derived from sucrose by replacing the hydroxyls in the 4, 1' and 6' positions with chlorine. Its sweetness is 600 times of sucrose. Sucralose does not take part in human metabolism, thus has high safety and high resistance to acid hydrolysis. These advantages allow it being the most favorable highly effective sweetener, and are approved by more than thirty countries for use already. The synthetic methods of sucralose used at present may be classified into two groups, i.e. full protection methods and single group protection methods, wherein the single group protection methods are adopted by most sucralose producers, which commonly use acetyl group as the blocking group. Accordingly, in the synthesis processes of the sucralose, the last step is naturally to remove this blocking group. The prior reports such as EP0043649, U.S. Pat. No. 4,380,476, JP57046995 and U.S. Pat. No. 6,809,198 all use sodium methoxide as a catalyst to proceed the deacylation reaction. By using these methods, the reaction proceeds mildly, and the operation is relatively simple. However, the conversion ratios of these methods are low. And inorganic salts are produced during reaction, which need to be adsorbed by ion exchange resin. Furthermore, since the PH of the reaction mixture decreases during the reaction process, additional catalyst is required to be supplied.

SUMMARY OF THE INVENTION

Aiming at the disadvantages of the aforementioned processes, the purpose of the present invention is to find out a method with higher conversion ratio, easier operation and more convenient post-treatment.

In order to realize the foregoing purpose, the present invention provides a process for the preparation of sucralose by the deacylation of trichlorosucrose-6-ethyl ester, said method comprising: dissolving trichlorosucrose-6-ethyl ester in an alcohol solvent; deacylating trichlorosucrose-6-ethyl ester in the presence of organic base catalyst; and after the completion of deacylation reaction, concentrating reaction mixture under reduced pressure and allowing it to crystallize, so as to obtain sucralose.

Specifically, the alcohol solvent useful in the present invention may be methanol or ethanol. The organic base catalyst(s) used in the present invention may be selected from a group consisted of triethylamine, diethylamine, tert-butylamine N-methylmorpholine and N-methylpiperidine. After the addition of the organic base catalyst(s), the PH of the reaction solution is controlled at about 9~13. And the reaction temperature is controlled in a range of from about 25° C. to about 80° C., depending on different catalysts and solvents.

The preparation process of the present invention goes as follows. Firstly, trichlorosucrose-6-ethyl ester is dissolved in an alcohol solvent. Organic base catalyst(s) is added into the solution to adjust PH of the solution. The deacylation reaction of trichlorosucrose-6-ethyl ester is conducted at appropriate temperature for several hours until trichlorosucrose-6-ethyl ester is completely deacetylated. The excess catalysts and solvents are distilled out under reduced pressure until a solid product is obtained, which is then dissolved in water and cooled down to obtain crystalline sucralose.

Compared with the reported methods for synthesis of sucralose by the deacylation of trichlorosucrose-6-ethyl ester, the present invention has the advantages of higher yield, easier operation, convenient post-treatment and higher purity of the final product.

The present invention will be further illustrated by the following examples, which however will not limit the present invention.

EXAMPLE 1

20 g of trichlorosucrose-6-ethyl ester was dissolved in 100 ml of methanol, and tert-butylamine was added into the solution thus obtained to adjust the PH of the solution to 12. The deacylation reaction of trichlorosucrose-6-ethyl ester is conducted at room temperature for 5 hours. And 1 g of active carbon was added into the reaction mixture, which was then stirred at room temperature for 30 minutes. The reaction mixture was filtrated, and excess tert-butylamine was removed from the filtrate at room temperature under vacuum. The filtrate was then gradually heated to 50° C. using a water bath. Methanol was distilled off under reduced pressure until a solid product was obtained, which was then added in 5 ml water and heated to 70° C. under stirring to completely dissolve sucralose. The solution thus obtained was then cooled down gradually to room temperature over 5 hours, allowed to crystallize, and then filtrated and dried to obtain 12.4 g of final product (yield: 68%).

EXAMPLE 2

20 g of trichlorosucrose-6-ethyl ester was dissolved in 100 ml of methanol, and triethylamine was then added into the solution thus obtained to adjust the PH of the solution to 13. The reactants was reacted under reflux for 7 hours, and then cooled down to 40° C. And 1 g of active carbon was added into the reaction mixture, which was stirred for 30 minutes and then cooled down to room temperature and filtrated. The methanol and excess triethylamine in the filtrate were distilled off under reduced pressure until a solid product was obtained, which was then added in 5 ml water and heated to 70° C. under stirring to completely dissolve sucralose. The solution thus obtained was then cooled down gradually to room temperature over 5 hours, allowed to crystallize, and then filtrated and dried to obtain 12.8 g of final product (yield: 70.8%).

EXAMPLE 3

20 g of trichlorosucrose-6-ethyl ester was dissolved in 120 ml of ethanol, and N-methylmorpholine was then added into the solution thus obtained to adjust the PH of the solution to 9.5. The reactants was reacted under reflux for 3 hours, and then cooled down to 40° C. And 1 g of active carbon was added into the reaction mixture, which was stirred for 30 minutes and then cooled down to room temperature and filtrated. The ethanol and excess N-methylmorpholine in the filtrate were distilled off under reduced pressure until a solid product was obtained, which was then added in 5 ml water and heated to 70° C. under stirring to completely dissolve sucralose. The solution thus obtained was then cooled down gradually to room temperature over 5 hours, allowed to crystallize, and then filtrated and dried to obtain 13.1 g of final product (yield: 72.4%).

What is claimed is:

1. A process for the preparation of sucralose consisting essentially of:
    dissolving trichlorosucrose-6-O-acetyl ester in an alcohol solvent;
    deacylating trichlorosucrose-6-O-acetyl ester in the presence of organic base catalyst; and
    after the completion of deacylation reaction, concentrating reaction mixture under reduced pressure and allowing it to crystallize, so as to obtain sucralose,
    wherein said organic base catalyst is tert-butylamine.

2. The process according to claim 1, wherein trichlorosucrose-6-O-acetyl ester has the following structure:

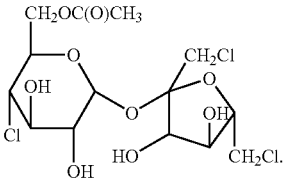

3. The process according to claim 1, wherein said alcohol solvent is selected from a group consisted of methanol and ethanol.

4. The process according to claim 1, wherein after the addition of the organic base catalyst, the pH is controlled in a range of from about 9 to about 13.

5. The process according to claim 1, wherein the reaction temperature is in a range of from about 25° C. to about 80° C.

* * * * *